United States Patent [19]

Elango et al.

[11] Patent Number: 4,981,995

[45] Date of Patent: Jan. 1, 1991

[54] METHOD FOR PRODUCING IBUPROFEN

[76] Inventors: Varadaraj Elango, 4175 Crenshaw, Corpus Christi, Tex. 78413; Mark A. Murphy, 3126 Dunbarton Oak, Corpus Christi, Tex. 78414; Brad L. Smith, 1034 Starlite, Portland, Tex. 78374; Kenneth G. Davenport, 38 Big Oak Dr., North Kingstown, R.I. 02852; Graham N. Mott, 7417 Lake Como, Corpus Christi, Tex. 78413; Edward G. Zey, 522 Evergreen, Corpus Christi, Tex. 78412; Gary L. Moss, 11113 Mulholland, Corpus Christi, Tex. 78410

[21] Appl. No.: 500,645

[22] Filed: Mar. 28, 1990

[51] Int. Cl.$^5$ .................. C07C 51/12; C07C 57/30
[52] U.S. Cl. ................................................ 562/406
[58] Field of Search ........................................ 562/406

[56]  References Cited

U.S. PATENT DOCUMENTS 4,843,172  6/1989  Tanaka et al. ...................... 562/406

FOREIGN PATENT DOCUMENTS 284310   9/1988  European Pat. Off. .
2242642 10/1982  Japan .
2242641 10/1987  Japan .
2263140 11/1987  Japan .

*Primary Examiner*—Paul J. Killos
*Attorney, Agent, or Firm*—Shirley L. Church

[57]  ABSTRACT

A method is provided for the preparation of ibuprofen by carbonylating 1-(4'-isobutylphenyl)ethanol (IBPE) with carbon monoxide in an acidic aqueous medium, e.g. containing at least 10% of water based on the weight of IBPE initially added, at a temperature of at least about 10° C. and a carbon monoxide pressure of at least about 500 psig, and in the presence of (1) a catalyst complex consisting essentially of a palladium compound in which the palladium has a valence of zero to 2 and is complexed with at least one monodentate phosphine ligand miscible with the organic phase of the reaction medium, the phosphorus/palladium mole ratio in said palladium compound and ligand being at least about 2:1 when the palladium/IBPE mole ratio is such that palladium=1 and IBPE=10,000 or more; (2) dissociated hydrogen ions from an acid which is substantially completely ionizable in dilute aqueous solution such that the mole ratio of hydrogen ions to IBPE added to the reaction zone is at least about 0.15; and, (3) dissociated halide ions such that the mole ratio of halide ions to IBPE added to the reaction zone is at least about 0.15. Advantageously, a hydrogen halide is the source of hydrogen ions and halide ions. The carbonylation is preferably integrated with a method of producing IBPE from isobutylbenzene wherein the latter compound is subjected to Friedel-Crafts reaction with an acetylating agent to produce 4-isobutylacetophenone, which is then reduced with hydrogen in the presence of a hydrogenation catalyst, or with a reducing agent containing available hydrogen, to obtain IBPE. The palladium catalyst complex can be precipitated from an organic phase of the carbonylation reaction which typically includes the ibuprofen product. The precipitated catalyst complex can be recycled without further treatment.

30 Claims, No Drawings

METHOD FOR PRODUCING IBUPROFEN

This application discloses and claims subject matter disclosed in Application Serial No. 07/357,381 of V. Elango et al., filed May 24, 1989 since abandoned which is a continuation-in-part of application Serial No. 07/158,141, filed March 4, 1988, also abandoned, which is a continuation-in-part of Application Serial No. 07/028,514 filed March 20, 1987, also now abandoned. This application also now discloses and claims subject matter disclosed in Application Serial No. 07/182,263, of Graham N. Mott et al., filed April 15, 1988, since abandoned. The subject matter of the above-referenced applications is being combined into a single continuation-in-part application.

FIELD OF THE INVENTION

This invention relates to an improved method for the production of 2-(4'-isobutylphenyl)propionic acid, more commonly known as ibuprofen. The invention includes the recovery and recycling of noble metal catalyst complexes useful in the production method.

BACKGROUND OF THE INVENTION

Ibuprofen is a well-known nonsteroidal anti-inflammatory drug which has been converted from ethical, i.e., prescription, to over-the-counter status. Various processes are known for the production of ibuprofen starting with 4-isobutylacetophenone. Thus, for example, British Patent No. 971,700 and corresponding U.S. Pat. No. 3,385,886, both assigned to Boots Company, PLC, show the production of arenealkane derivatives such as ibuprofen in which the first step of the process is the reaction of a arenealkane with acetyl chloride in the presence of aluminum chloride to produce an alkylacetophenone which is then subjected to any of various series of subsequent reactions to produce the desired derivative.

α-arylpropionic acids, in general, have been formed by the carbonylation of the respective arylethyl alcohol. For example, Japanese Kokai Patent No. SHO 55 [1980]-27147, published Feb. 27, 1980 and assigned to Mitsubishi Petrochemical Co., discloses the formation of ibuprofen by reacting 1-(4'-isobutylphenyl)ethanol with carbon monoxide and water in the presence of a hydrogen fluoride catalyst. Japanese Kokai Patent No. SHO 59 [1984]-95238, published June 1, 1984 and assigned to Mitsubishi Petrochemical Co., teaches the formation of alpha-aryl-sustituted propionic acids, where the aryl group may be a phenyl group containing at least one alkoxy, aryloxy, hydroxy, or amino group as an electron-donor substituent, by reacting a benzyl alcohol derivative, which may be an α-aryl substituted ethanol wherein the aryl group is the same as in the phenylacetic acid derivative product, with carbon monoxide and water, alcohol, or phenol, in the presence of a palladium catalyst. An acidic compound such as hydrogen chloride may be added as an auxiliary catalyst and a solvent such as benzene may also be used. The disclosure includes a comparative example in which ibuprofen (not included within the invention) is obtained in very low yield, i.e., 17.1%, when made utilizing the described process. Japanese Kokai Patent No. SHO 59 [1984]-95239, published June 1, 1984 and assigned to Mitsubishi Petrochemical Co., discloses the formation of α-(6-methoxy-2-naphthyl)propionic acid by reacting α-(6-methoxy-2-naphthyl)ethyl alcohol with carbon monoxide and water in the presence of a palladium catalyst and an acidic compound, e.g., hydrogen chloride. The patent publication also states that if a non-halogen-containing acidic compound is used, it is desirable to add an ionizable metal halide to the reaction.

Japanese Kokuku Patent No. SHO 56 [1981]-35659, published Sept. 4, 1978 and assigned to Ferrel International Societe Annonim, discloses an anhydrous method of producing a 2-(4'-isobutylphenyl)propionic acid ester by treating 1-(4'-isobutylphenyl)ethanol (IBPE) with carbon monoxide in a solution containing an alkanol and a catalyst such as palladium bis(triphenylphosphine) dichloro complex. The solution may also contain up to 10% of a mineral acid such as hydrogen chloride.

British Patent 1,565,235, assigned to Mitsubishi Petrochemical Co. discloses a process for producing alpha-arylpropionic acids which have an anti-inflammatory, analgesic or antipyretic effect. The process comprises reacting an arylethylene with carbon monoxide under pressure in the presence of a carbonylation catalyst and in the presence of water and/or a lower alcohol to carbonylate the arylethylene to produce the alpha-aryl propionic acid. The starting materials for the arylethylenes can be prepared such as by the dehydration of arylethyl alcohols or by the dehydrohalogenation of arylethyl halides. The arylethylenes can be purified by means of a single distillation or recrystallization to obtain the products with a sufficiently high purity to be used as the starting material for the subsequent carbonylation step.

Baddely et al., Journal of the Chemical Society, 4943-4945 [1956], discloses on page 4945 the preparation of 4-isobutylacetophenone by the Friedel-Crafts acetylation of isobutylbenzene with acetyl chloride using aluminum chloride as catalyst.

Japanese Patent Publication (Early Disclosure) No. 60 [1985]-188,643, discloses the preparation of p-isobutylacetophenone by the ac®tylation of isobutylbenzene using as an acetylating agent acetyl fluoride prepared by reacting acetic anhydride with hydrogen fluoride as a catalyst, or a combination of hydrogen fluoride and boron trifluoride as a catalyst.

SUMMARY OF THE INVENTION

In accordance with this invention, 2-(4'-isobutylphenyl)propionic acid, i.e., ibuprofen, is prepared by carbonylating 1-(4'-isobutylphenyl)ethanol (IBPE) with carbon monoxide while in contact with an acidic aqueous medium at a temperature of at least about 10° C and a carbon monoxide pressure of at least about 500 psig, and in the presence of (1) a catalyst consisting essentially of a palladium compound in which the palladium has a valence of zero to 2 and is complexed with at least one acid stable, monodentate phosphine ligand freely miscible with the organic phase of the reaction medium, the phosphorus/ palladium mole ratio in said palladium compound and ligand being at least about 2:1 when the mole ratio of palladium to IBPE is such that palladium=1 and IBPE=10,000 or more; (2) dissociated hydrogen ions from an acid which is substantially completely ionizable in a dilute aqueous solution, e.g., of 0.1N concentration, such that the mole ratio of hydrogen ions to IBPE added to the reaction zone ($H^+$/IBPE) is at least about 0.15; 3) dissociated halide ions such that the mole ratio of halide ions to IBPE added to the reaction zone ($X^-$/IBPE) is at least about 0.15.

The preferred mole ratio of hydrogen ions to water (H₃O/H₂O), corresponding with the H+/*IBPE mole ratio of at least about* 0.15, is at least about 0.026.

The term "monodentate" is intended to mean a single phosphine phosphorus atom present in the ligand molecule before it is complexed with palladium. The phrase "freely miscible with the organic phase of the reaction medium" means that the ligand is not complexed with an insoluble substrate such as a polymer which prevents it from being freely mixed in the organic phase.

The carbonylation reaction proceeds in accordance with equation (I):

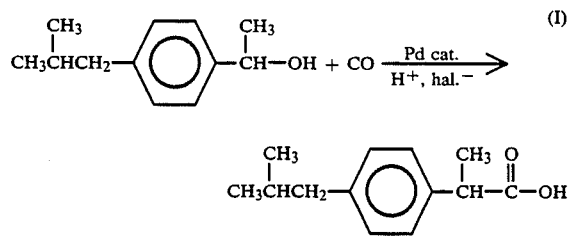

In carrying out the carbonylation reaction, water may be present in an amount, for example, of about 10 to 600%, preferably about 15 to 100%, based on the weight of IBPE initially present; the temperature of reaction may be, for example, in the range of about 10 to 225.C., preferably about 70 to 175.C; the carbon monoxide pressure may be, for example, in the range of about 500 to 5000 psig, preferably about 700 to 3000 psig; and the total reaction time may be, for example, in the range of about 0.1 to 24 hours, preferably about 1 to 6 hours.

Some palladium catalysts which may be used wherein the palladium is complexed with an appropriate ligand are as follows: bis(triphenylphosphine) dichloro complex, bis(tributylphosphine) dichloro complex, bis(tricyclohexylphosphine) dichloro complex, pi-allyltriphenylphosphine dichloro complex, triphenylphosphine piperidine dichloro complex, bis(triphenylphosphine) dicarbonyl complex, bis(triphenylphosphine)-diacetate complex, bis(triphenylphosphine) dinitrate complex, bis(triphenylphosphine) sulfate complex, tetrakis(triphenylphosphine) complex, and complexes in which some of the ligands are carbon monoxide such as chlorocarbonyl bis(triphenylphosphine) complex, all complexes of palladium. Also suitable as a catalyst is palladium metal on a suitable catalyst support such as carbon, alumina, silica, or an inert polymer which can tolerate the conditions of reaction, complexed with one or more of these foregoing ligands.

The palladium salts and phosphine ligands making up the foregoing catalyst complexes may also be added separately to the reaction zone. In this case, the amount of ligand added is preferably sufficient to complex with the palladium present such that the P:Pd mole ratio is equal to at least about 1:1 when the Pd:IBPE mole ratio is at least about 1:5,000. However, when the latter ratio is such that Pd=1 and IBPE=10,000 or more (1:10,000 or greater than 10,000), it is necessary to use an excess of phosphine ligand such that the P:Pd ratio is at least about 2:1.

The catalyst complex may be present in an amount such that the mole ratio of palladium to IBPE is in the range, for example, of about 1:25 to 1:60,000, preferably about 1:150 to 1:30,000, and most preferably about 1:1000 to 1:5,000.

The dissociated hydrogen ions and halide ions may be conveniently added to the reaction as hydrogen chloride, hydrogen bromide, or hydrogen iodide. However, it is also possible to add the hydrogen ions and halide ions from separate sources. For example, other acids completely ionizable in dilute aqueous solution, e.g., inorganic acids, such as sulfuric acid, phosphoric acid or polyphosphoric acid, or organic acids, e.g., sulfonic acids such as p-toluenesulfonic acid, methanesulfonic acid, or trifluoroacetic acid, may be used as the source of hydrogen ions. Similarly, other water-soluble and ionizable halide compounds, as for example, halide salts wherein the cation does not interfere with the reaction, e.g., alkali metal halides such as potassium, sodium, and lithium chlorides, bromides, and iodides may be used as the source of halide ions. The mole ratio of hydrogen ions and halide ions to IBPE (H+/IBPE and X−/IBPE) each may be in the range, for example, of about 0.15 to. 5, preferably about 0.3 to 2.0.

Although not necessary for the operability of the process, in some instances, it may be advantageous to utilize an organic solvent for the reaction. Organic solvents which can be used are, for example, ketones such as methyl ethyl ketone, acetone, 2-pentanone, 3-pentanone, and acetophenone, aromatic hydrocarbons such as benzene and toluene, and cyclic ethers such as tetrahydrofuran and dioxane. Ketones and ethers are preferred if a solvent is used. If the catalytic palladium as added to the system is in the metallic or zero valence state (Pd°), then any solvent used should be non-hydrocarbon. The solvent may be present in a weight ratio of solvent to IBPE ranging, for example, from about 0 to 1000:1, preferably from about 0 to 10:1.

An inorganic salt may also be present during the reaction. Inorganic salts which may be used are, for example, those yielding anions comprising oxygen, and sulfur, phosphorus, aluminum, or silicon, including such anions as hydrogensulfate, pyrosulfate, ortho-phosphate, pyrophosphate, aluminate, or silicate and cations such as sodium, potassium, calcium, or magnesium, or another cation which does not interfere with the reaction, e.g., ammonium or alkylammonium such as tetrabutylammonium. Other inorganic salts such as calcium chloride may also be added. The inorganic salt, if used, will generally be present at a concentration of, for example, about 0.1 to 50%, preferably about 1 to 20% by weight of total charge.

In addition to those mentioned previously, other additives and ligands may be added to the reaction, e.g., acetophenone and substituted acetophenones such as p-mercaptoacetophenone.

In some instances, an undesirable heavy ends fraction may form during the reaction, possibly due to a polymerization mechanism of unknown nature. In view of this, it may be beneficial to incorporate a polymerization inhibitor in the reaction mass. Inhibitors which may be used for this purpose include, for example, t-butylcatechol, hydroquinone, m-dinitrobenzene, N-nitrosodiphenylamine, picric acid, sodium sulfite, hydroquinone and the like. If an inhibitor is utilized, it may be incorporated in an amount, for example, of about 0.01 to 15%, preferably about 0.1 to 5% by weight based on the weight of IBPE.

The IBPE used to produce ibuprofen in accordance with the method of this invention may be made by any of various means. Preferably, however, the carbonylation reaction to produce ibuprofen is integrated with a method of producing IBPE from isobutylbenzene wherein the latter compound is subjected to Friedel-Crafts reaction with an acetylating agent to produce 4-isobutylacetophenone (IBAP) which is then reduced with hydrogen in the presence of a hydrogenation catalyst, or with a reducing agent containing available hydrogen, to obtain IBPE.

The Friedel-Crafts acetylation of isobutylbenzene to produce 4-isobutylacetophenone proceeds in accordance with equation (II):

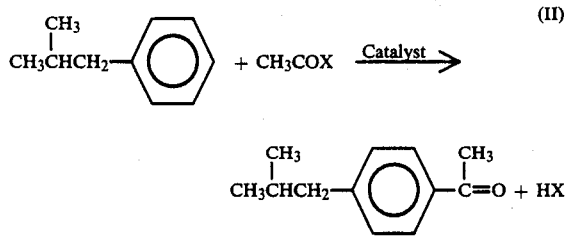

where X is the residue minus an acetyl group of compounds which are known acetylating agents. X may be, for example, hydroxy, acetoxy, or halide including chloride, fluoride, or bromide. Acetylating agents which may be used are for example acetic acid, acetic anhydride, acetyl fluoride, acetyl chloride, acetyl bromide, and ketene, which results from the abstraction of HX from the foregoing acetylating agents prior to the acetylation reaction. The acetylating agent may be used in an amount, for example, of about 1 to 4 moles, preferably about 1.1 to 2.0 moles per mole of isobutylbenzene employed.

The Friedel-Crafts catalyst may be hydrogen fluoride or any other catalyst known in the art to be effective for the Friedel-Crafts reaction, e.g., aluminum chloride, zinc chloride, or boron trifluoride. In carrying out the reaction, isobutylbenzene, acetylating agent, and catalyst, may be charged to a corrosion-resistant reactor and the mixture maintained at a temperature, for example, of about 0 to about 120° C, for a period, for example, of about 0.5 to about 5 hours. The pressure is not critical and atmospheric or autogenous pressure may be utilized. If HF is used as the catalyst, it may be charged as a liquid or a gas using technologies of handling well-known to those skilled in the art. In carrying out the reaction, an inert gas such as nitrogen may be used to keep sufficient HF in contact with the reacting liquid. An excess of HF is generally used, for example, about 10 to 100 moles, preferably about 25 to about 75 moles per mole of isobutylbenzene initially present in the reaction zone.

The hydrogenation or reduction of IBAP to form IBPE proceeds in accordance with equation (III) where "[H]" represents the available hydrogen in hydrogen gas in the presence of a hydrogenation catalyst or in a hydrogen-containing reducing agent such as sodium borohydride or lithium aluminum hydride:

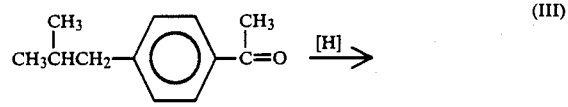

-continued

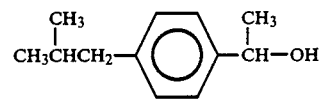

The hydrogenation or reduction as shown in equation (III) may be accomplished, for example, by contacting IBAP as is or dissolved in an appropriate solvent with a hydrogenation catalyst in the presence of hydrogen. The solvent may be, for example, methanol, ethanol, t-butanol, aqueous alcohol, toluene, diethyl ether, tetrahydrofuran, or 1,4-dioxane, and the IBPE: solvent weight ratio may be in the range, for example of about 1:1 to 1:100, preferably about 1:2 to 1:20. The hydrogenation catalyst may be, for example, a transition metal on a suitable support. Preferred transition metals are nickel, e.g., Raney nickel, and other Group VIII B noble metals, e.g., palladium, platinum, rhodium, iridium, and ruthenium, and some suitable supports are, for example, carbon, alumina, silica, and polymeric resins. The metal concentration on the support in weight ratio of metal:support may be in the range, for example, of about 1:100 to 1:2, preferably about 1:50 to 1:10, and the weight ratio of catalyst system:IBAP is, for example, in the range of about 1:500 to 1:2, preferably about 1:30 to 1:5. In carrying out the reaction, the hydrogen pressure may be in the range, for example, of about 10 to 1200 psig, preferably about 75 to 300 psig; the reaction temperature may be in the range, for example, of about 10 to 150° C., preferably about 20 to 80° C.; and the reaction time may be in the range, for example, of about 0.25 to 10.0 hours, preferably about 1.0 to 4.0 hours. Under some conditions, the addition of a base or passivation of the reactor with base, may be desirable to prevent hydrogenolysis.

Alternative to the hydrogenation reaction as described, the reduction reaction shown in equation (III) may be accomplished, for example, by slowly adding to a cooled solution of IBAP in an alcohol, e.g., methanol, ethanol, or t-butanol, or an ether such as tetrahydrofuran or diethyl ether, a reducing agent containing available hydrogen, e.g., sodium or potassium borohydride or lithium aluminum hydride. The solution may then be warmed to room temperature and heated at reflux, e.g., for a period of about 0.5 to 3.0 hours.

In the carbonylation of IBPE to ibuprofen, it would be worthwhile to recover and recycle the palladium catalyst complex in relatively pure form from the ibuprofen reaction products, in view of the cost of the carbonylation catalyst. Similarly, it would be highly advantageous to maintain high conversion, high selectivities and high yields even after recycling the catalyst several times. It would also be useful to recover the catalyst by means which does not degrade or decompose the catalyst. Recovery and recycle of a sufficiently pure palladium catalyst has been attempted in other chemical industry processes with limited success; the recovery being dependent on the particular variables of the process involved. Typically, a sufficient amount of a catalyst sludge is eventually formed and is returned to the reactor, see U.S. 3,455,989. As disclosed in U.S. 4,013,583, a palladium complex catalyst used in the carbonylation, hydroformylation and hydrogenation of olefins was recovered and regenerated. Recovery of the palladium carbonylation catalyst was achieved by dispersing the ligandstabilized palladium halide catalyst in quaternary ammonium, phosphonium or arsonium salts of trihalostannate or trihalogermanate. However, the palladium catalyst recovered then contained the stannate or germanate component.

It has now been discovered that in the carbonylation of 1-(4-isobutylphenyl)ethanol (IBPE) to 2-(4'-isobutylphenyl)propionic acid, i.e., ibuprofen, in an acidic aqueous medium, the carbonylation catalyst consisting essentially of palladium halide, complexed with a triorganophosphine ligand, can be precipitated from the reaction products in substantially pure form and recycled directly to the carbonylation reactor. Precipitation of the catalyst is not induced by the addition of extraneous agents as in U.S. 4,013,583, which agents may adversely effect catalysis and the nature of the product formed.

In accordance with the present invention, the palladium complex catalyst used in the carbonylation of IBPE to ibuprofen according to equation (I) is precipitated in substantially pure form and can be collected for recycle to the carbonylation reaction. It is believed that the unique mixture of carboxylic acids including ibuprofen in the product, and the remaining organic medium such as solvent allows for the formation and ultimate precipitation of the phosphine ligand-stabilized palladium complex catalyst without the addition of a separate complexing agent which may alter in a significant way the chemical composition of the catalyst complex.

Upon completion of the carbonylation reaction such as by equation (I), a reaction product is formed which contains two separate liquid phases. The heavier aqueous phase contains the dissociated hydrogen and halide ions while the lighter organic phase contains the ibuprofen product, organic by-products, any solvent and the soluble palladium complex catalyst. To recover the catalyst, the aqueous and organic phases must be separated. Separation of the phases can be done by well-known techniques such as by decantation from a separatory funnel and the like. If the phases are not well defined on completion of the carbonylation reaction, an organic solvent can be added to improve phasing. For example, in a reaction medium which contains a ketone solvent such as methyl ethyl ketone, the addition of ethyl acetate has been found to greatly improve the phase separation between the aqueous and organic phases. The amount of phasing organic solvent added to enhance phase separation can vary widely but, will typically range from about 0.1 to 10 parts volume per part volume of liquid reaction medium. The aqueous phase once separated can be returned directly to the carbonylation reactor, any suspended metallic Pd° remaining in the aqueous phase after precipitation of the palladium catalyst complex can be recovered by filtration of the aqueous phase.

If a solvent has not been used in the carbonylation reaction, the phosphine ligand-stabilized palladium catalyst will precipitate out of the organic phase in essentially pure form. This precipitate can be collected and recycled directly to the carbonylation reactor. No treatment of the catalyst precipitate is needed prior to recycle.

If a solvent has been used in the carbonylation reaction, the solvent must be removed before precipitation takes place. Removal of solvent from the organic phase can be done in various ways such as by extraction or by distillation. Further, certain solvents useful in the carbonylation are good coordinating solvents and serve as ligands which form a tightly bound complex with the palladium catalyst. Ketones are examples of good coordinating solvents. Thus, if a coordinating solvent has been used, a noncoordinating solvent can be added to disengage the coordinating solvent from the palladium phosphine complex catalyst. Upon addition of the noncoordinating solvent, the palladium phosphine complex catalyst precipitates from the organic phase. The amount of noncoordinating solvent added to precipitate the palladium complex will also vary widely depending on the solvents used during the carbonylation. In general, about 0.1 to 10 parts volume of noncoordinating solvent per part volume of organic phase will disengage the solvent ligand and provide for precipitation of the palladium-phosphine complex catalyst. An example of a useful solvent which coordinates with the palladium complex catalyst is methyl ethyl ketone. Examples of noncoordinating solvents include esters such as ethyl acetate; nonaromatic hydrocarbons such as hexane and heptane; and aromatic hydrocarbons such as benzene and toluene. The addition of ethyl acetate to the organic phase containing the methyl ethyl ketone initiates precipitation of the phosphine ligand stabilized palladium halide complex catalyst at about 70.C to 80.C. In each case, whether or not a coordinating solvent is present or whether the solvent is removed or a noncoordinating solvent is added, the palladium halide complex catalyst typically can be precipitated over a temperature range of about 0° C to 100° C with a preferred temperature range of 25.C to 90.C and thus, some cooling may be required.

Carbonylation of IBPE to ibuprofen with the recycled aqueous phase and palladium catalyst does not require any change in process conditions. It is only necessary to add make-up hydrogen and halide ions to the aqueous phase and provide for make-up catalyst. It has been found that about 90% of the palladium catalyst will precipitate and can be recovered for recycle.

Thus, in accordance with the present invention, ibuprofen is prepared by carbonylating 1-(4,-isobutylphenyl)ethanol with carbon monoxide under the process conditions set forth above, in which the carbonylation catalyst is palladium halide complexed with triorganophosphine. The carbonylation reaction takes place at a temperature of at least about 10° C and a carbon monoxide pressure of at least about 500 psig and in the presence of 1) the palladium complex catalyst; 2) dissociated hydrogen ions such that the molar ratio of hydrogen ions to IBPE added to the reaction zone is at least about 0.15; 3) dissociated halide ions such that the molar ratio of halide ions to IBPE present in the reaction zone is at least about 0.15 and 4) optionally an organic solvent. Upon completion of the reaction, two phases are formed, an aqueous phase containing the dissociated hydrogen and halide ions and an organic phase containing the ibuprofen, byproducts and solvent, if used. The aqueous phase is removed by known separatory techniques and returned to the reactor. Upon removal of any solvent from the organic phase, the palladium halide complex catalyst precipitates from the organic phase in substantially pure form and can be collected and recycled directly to the carbonylation reactor.

DESCRIPTION OF PREFERRED EMBODIMENTS OF THE INVENTION

Examples 1 to 105, which follow, illustrate the method of the invention related to the overall improved method for production of ibuprofen. Comparative Examples A to L illustrate conditions and results wherein at least one condition is outside the scope of the invention.

Example 1 illustrates the production of IBAP by the Friedel-Crafts acetylation of isobutylbenzene with acetic anhydride as acetylating agent in accordance with equation (II), wherein X is acetoxy.

EXAMPLE 1

Isobutylbenzene (254 g, 1.9 mol) and acetic anhydride (385 g, 3.8 mol) were added to a Hastelloy C autoclave which was then cooled to 5.C and evacuated (150 mm HgA). Anhydrous hydrogen fluoride (1877 g, 94 mol) was added and the contents of the autoclave were warmed to 80° C for 3 h. The hydrogen fluoride was vented through a caustic scrubber using a nitrogen sparge. The contents of the autoclave were poured onto ice, neutralized to a pH of 7 with potassium hydroxide, and extracted with ethyl acetate. The ethyl acetate solution was dried over anhydrous magnesium sulfate and concentrated under reduced pressure to give the crude product. The reaction was determined by gas-liquid chromatography (GLC) to have proceeded with 85% conversion of isobutylbenzene and 81% selectivity to IBAP.

Example 2 illustrates the production of IBPE by the hydrogenation of IBAP using palladium supported on carbon as a hydrogenation catalyst in accordance with equation (III), and employing methanol as a solvent.

EXAMPLE 2

A 300 cc stainless steel autoclave was charged with 4-isobutylacetophenone (IBAP) (35.2 g, 0.2 mole), 100 ml of methanol, and 5 g of 5% palladium/carbon catalyst. The contents of the autoclave were warmed to 30.C under 100 psig of hydrogen for 1 h. The resulting mixture was filtered and the methanol was removed on a rotary evaporator. The reaction was determined by GC to have proceeded with 99.5% conversion of IBAP and 96.6% selectivity to IBPE.

Example 3 shows the production of IBPE by the hydrogenation of IBAP using a procedure similar to Example 2 except that no solvent was employed.

EXAMPLE 3

A 500 cc reactor Was charged with IBAP (225 g, 1.26 mol), 5% Pd/C (10 g, 4.7 mmol), and 2N NaOH (0.2 ml). The autoclave was purged three times with $N_2$ (100 psig) and twice with 100 psig $H_2$. It was pressured to 125 psig with $H_2$ and the contents were stirred at room temperature until $H_2$ absorption ceased. The catalyst was filtered using a small column of celite. GLC analysis of the crude mixture showed 92% IBPE and 6.2% 1-(4'-isobutylphenyl)ethane. The mixture was purified by distillation under reduced pressure (bp=85–88° C. at 0.5 mm HgA) to give 96–97% pure IBPE.

Example 3A illustrates the production of IBPE by the hydrogenation of IBAP in accordance with equation (III), using Raney nickel as hydrogenation catalyst, and in the absence of a solvent.

EXAMPLE 3A

A 500 cc stainless steel autoclave was charged with IBAP (225 g, 1.26 mol) and Raney nickel (22.5 g 0.38 mol). The reactor was purged three times with $N_2$ (100 psig) and twice with 100 psig Hz. It was pressured with Hz at 70.C until $H_2$ absorption ceased (about 3 hours). The resulting mixture was filtered. GLC analysis of the crude mixture indicated >99% IBPE conversion with selectivities of 98% and 1.5% to IBPE and 1-(4'isobutylphenyl)ethane respectively.

Examples 4 to 98 illustrate the inventive method for producing ibuprofen by the carbonylation of IBPE while Examples A to L are outside the scope of the invention.

EXAMPLES 4 and 5

1-(4'-Isobutylphenyl)ethanol (IBPE) (10.0 g, 56.0 mmol), $PdCl_2(PPh_3)_2$ (260 mg. 0.37 mmol), 10% HCl (25 g, 68 mmol HCl, $H_3O$ /$H_2O$=0.055) and benzene (27 ml) were charged to a 300 cc Hastelloy C autoclave which was sealed and purged twice with $N_2$ and CO. The autoclave was pressured to 800 psig with CO and the contents were heated to 125–129° C. for 16 h (Example 4), or 6 h (Example 5), with stirring. The autoclave was cooled to room temperature, vented of CO, and the sample was collected. The organic layer was separated from the aqueous layer which was washed with ethyl acetate (75 ml). The organic fractions were combined, dried over anhydrous sodium sulfate, and concentrated under reduced pressure to give a greenish oily product.

EXAMPLES 6 to 10

The procedure of Examples 4 and 5 was followed except that 11 mmol each of fused potassium hydrogen sulfate (Example 6), sulfuric acid (Example 7), polyphosphoric acid (Example 8), 11 mmol of potassium hydrogen sulfate and 0.6 mmol of tetrabutylammonium hydrogen sulfate (Example 9), or 8 mmol of calcium chloride (Example 10), were also charged to the autoclave and 27 ml of methyl ethyl ketone in place of benzene in Example 10. In addition, 2.8 mmol of acetophenone were also added in Examples 7, 8 and 9, and 0.3 mmol of t-butylcatechol in Example 9. The reaction time was 19 h in Examples 6, 7 and 8, and 6 h in Examples 9 and 10.

N-7043C

The products obtained in Examples 4 to 10 were analyzed by GLC for ibuprofen, 3-(4'-isobutylphenyl)-propionic acid, which is a linear isomer of ibuprofen (3-IPPA), 4-isobutylstyrene (IBS), and a heavy ends component (HE) which is believed to comprise polymers of 4-isobutylstyrene as well as other high boiling compounds. The results are shown in Table I wherein "Conv." indicates percent conversion of IBPE and the numbers under the product component designations are percent selectivities to those components, with the symbol "tr" indicating a trace of that component.

TABLE I

| | | Percent Selectivity | | | |
| Example | Conv. % | Ibuprofen | 3-IPPA | IBS | HE |
| --- | --- | --- | --- | --- | --- |
| 4 | 98 | 56 | 26 | tr | 4 |
| 5 | 99 | 56 | 21 | tr | 7 |
| 6 | 99 | 69 | 18 | 0 | 6 |
| 7 | 98 | 69 | 15 | tr | 5 |
| 8 | 99 | 70 | 16 | 0 | 4 |
| 9 | 100 | 67 | 21 | tr | 4 |
| 10 | 99 | 78 | 23 | tr | 4 |

COMPARATIVE EXAMPLES A TO F

These examples illustrate the effect of not having the required quantity of both dissociated hydrogen ions and halide ions under the invention (Examples A and B), not having sufficient hydrogen ions (Examples C and D), not having sufficient hydrogen ions obtained from an acid which is substantially completely ionized in dilute aqueous solution (Example E) or not having sufficient halide ions (Example F).

The procedure of Example 6 was followed except that water (25 g) (Examples A to E) or 29% $H_2SO_4$ (27 ml) (Example F), was used in place of 10% HCl. In addition, no potassium hydrogen sulfate was used in Example F; 27 ml of acetic acid was used in place of benzene in Example E; 10 mmol of lithium chloride in Example C, 24 mmol of lithium chloride in Example D and 69 mmol of potassium chloride in Example E were charged to the autoclave as a source of chloride ions; and 0.3 mmol of t-butylcatechol in Examples A to D, 28 mmol of acetophenone in Examples B and D, and 3.2 mmol of p-mercaptoacetophenone in Example E, were also added. The reaction times were 6 h in Examples A, E and F, 8 h in Example B, 7 h in Example C, and 48 h in Example D. The results are shown in Table II:

TABLE II

| Example | Conv. % | Percent Selectivity | | | |
|---|---|---|---|---|---|
| | | Ibuprofen | 3-IPPA | IBS | HE |
| A | 33 | 0 | 0 | 8 | 7 |
| B | 19 | tr | 0 | 2 | 4 |
| C | 64 | 0 | 0 | 7 | 19 |
| D | 68 | 3 | tr | 6 | 37 |
| E | 99 | 23 | 54 | 2 | 7 |
| F | 97 | 5 | 3 | 12 | 69 |

The results of Table II indicate that a minimum quantity of both dissociated hydrogen ions obtained from an acid which is substantially completely ionized in dilute aqueous solution, and halide ions are necessary for substantial yields of ibuprofen, and that reaction times of more than 15 to 20 h will probably not serve to increase the yield.

EXAMPLES 11 to 13

These examples illustrate the use of sulfuric acid as the source of dissociated hydrogen ions instead of HCl.

The procedure of Example 6 was followed except that the 10% HCl was replaced by 40% sulfuric acid (25 g, 102 mmol, $H_3O/H_2O=0.123$) in Example 11, or 28.4% sulfuric acid (25 g, 71 mmol, $H_3O/H_2O=0.073$) in Examples 12 and 13, and no potassium hydrogen sulfate was added in Examples 11. In addition, 70 mmol of sodium chloride were added in Example 11, 69 mmol of potassium chloride were added in Examples 12, and 69 mmol of potassium bromide were added in Example 13 as sources of halide ions; 25 ml of acetonitrile were used in Example 12 and 25 ml of methyl ethyl ketone in Example 13 as solvent replacements for benzene; and 0.3 mmol of t-butylcatechol were added in Example 12, and 2.8 mmol of acetophenone were added in Examples 11 and 13. The reaction times were 19 h in Example 9, and 6 h in Examples 12 and 13. The results are shown in Table III:

TABLE III

| Example | Conv. % | Percent Selectivity | | | |
|---|---|---|---|---|---|
| | | Ibuprofen | 3-IPPA | IBS | HE |
| 11 | 99 | 70 | 16 | 0 | 4 |
| 12 | 96 | 42 | 6 | tr | 34 |
| 13 | 99 | 69 | 9 | tr | 10 |

The results of Table III indicate that sulfuric acid is a satisfactory source of hydrogen ions, that halide salts are an effective source of halide ions and that acetonitrile is a less desirable solvent than others because of its tendency to form heavy ends at the expense of ibuprofen.

EXAMPLES 14 TO 17

These examples illustrate the use of HBr as a source of dissociated hydrogen ions and halide ions.

The procedure of Example 6 was followed except that a 16.2% HBr (25 g, 50 mmol, $H_3O^+/H_2O=0.044$) Was used in Examples 14, 15 and 16 and a 22.7% HBr (25 g, 70 mmol, $H_3O/H_2O=0.065$) was used in Example 17 in place of 10% HCl as a source of hydrogen ions and halide ions; methyl ethyl ketone (27 ml) was used as solvent in Examples 16 and 17; 3.0 mmol of t-butylcatechol was added in Example 14 and 3.2 mmol of p-mercaptoacetophenone in Example 15; and the reaction times were 6 h in Examples 14, 15 and 17, and 5.3 h in Example 16. The results are given in Table IV:

TABLE IV

| Example | Conv. % | Percent Selectivity | | | |
|---|---|---|---|---|---|
| | | Ibuprofen | 3-IPPA | IBS | HE |
| 14 | 100 | 85 | 8 | tr | 5 |
| 15 | 99 | 59 | 3 | 13 | 10 |
| 16 | 100 | 62 | 14 | 0 | 6 |
| 17 | 100 | 69 | 8 | tr | 12 |

The results of Table IV indicate that HBr is a satisfactory source of hydrogen ions and halide ions for purposes of this invention.

EXAMPLE 18

The procedure of Example 17 was followed except that 34 g of 24% methanesulfonic acid ($H_2O/H_2O=0.059$) was utilized as the source of dissociated hydrogen ions in place of the HBr solution and 69 mmol of sodium bromide was added as a source of halide ions. The conversion of IBPE was 99% and the selectivities of the product components were ibuprofen 71%, 3-IPPA 13%, IBS "tr", and HE 8%.

The results of this example indicate that methanesulfonic acid is a satisfactory source of dissociated hydrogen ions for purposes of this invention.

EXAMPLES 19 TO 22

These examples illustrate the use of various additives to the reaction system, as discussed previously.

The procedure of Example 6 was followed except that 0.3 mmol of t-butylcatechol was added in Examples 19, 20, 21, and 22, 2.8 mmol of acetophenone in Examples 20, 21, and 22, and 3.2 mmol of p-mercaptoacetophenone in Example 22; and the reaction times were 15 h in Example 19, 20 h in Examples 20 and 21, and 19 h in Example 22. The results are shown in Table V:

TABLE V

| Example | Conv. % | Percent Selectivity | | | |
|---|---|---|---|---|---|
| | | Ibuprofen | 3-IPPA | IBS | HE |
| 19 | 98 | 49 | 20 | 0 | 6 |
| 20 | 98 | 74 | 7 | 0 | 4 |
| 21 | 98 | 69 | 5 | 0 | 3 |
| 22 | 100 | 82 | 4 | tr | 8 |

EXAMPLES 23 TO 30

These examples illustrate the use of different solvents in the method of this invention.

The procedure of Example 6 was followed except that the benzene solvent was replaced by 27 ml each of other solvents as follows: toluene (Example 23), tetrahydrofuran (Example 24), dioxane (Examples 25 and 26), acetone (Example 27), methyl ethyl ketone (Example 28), and acetonitrile (Examples 29 and 30), and 36 g of 10% HCl was used in Example 25. In addition, 0.3 mmol of t-butylcatechol were added in Examples 23 to 25, 29 and 30, 2.8 mmol of acetophenone were added in Examples 23 to 25 and 30, and 3.2 mmol of p-mercaptoacetophenone were added in Examples 26 and 27; and the reaction times were 6 h in Examples 23 to 29 and 19 h in Example 30. The results are shown in Table VI:

TABLE VI

| Example | Conv. % | Percent Selectivity | | | |
|---|---|---|---|---|---|
| | | Ibuprofen | 3-IPPA | IBS | HE |
| 23 | 99 | 43 | 16 | tr | 20 |
| 24 | 99 | 56 | 14 | tr | 9 |
| 25 | 99 | 76 | 12 | 0 | 11 |
| 26 | 99 | 65 | 13 | 1 | 18 |
| 27 | 99 | 75 | 21 | tr | 4 |
| 28 | 99 | 72 | 18 | tr | 6 |
| 29 | 97 | 48 | 7 | tr | 40 |
| 30 | 95 | 26 | 9 | tr | 47 |

The results of Table VI indicate that a variety of solvents can be used in the method of this invention. However, ketones and cyclic ethers appear to result in higher yields of ibuprofen than acetonitrile which tends to cause the formation of a larger amount of heavy-ends than the other solvents.

COMPARATIVE EXAMPLE G

This example illustrates the effect of reducing reaction pressure below the minimum required by this invention.

The procedure of Example 6 was followed except that the reaction was charged with 400 psig of CO at room temperature. In addition 3.2 mmol of p-mercaptoacetophenone was added and the reaction time was 6 h. The conversion of IBPE was 97% and the selectivities of the product component were ibuprofen 20%, 3-IPPA 3%, IBS 24% and HE 19%. These results indicate that using a pressure below 500 psig results in a substantial reduction in the yield of ibuprofen and an increase in the formation of 4-isobutylstyrene.

EXAMPLES 31 AND 32 AND COMPARATIVE EXAMPLES H TO J

These examples illustrate the effects of varying the composition of the catalyst.

The procedure of Example 16 was followed except that the reaction time was 6 h in Examples 31, 32, I, and J, and 4.5 h in Example H; the catalyst was 0.44 mmol of PdCl$_2$ and 1.9 mmol of triphenyl phosphine (PPh3) added separately in Example 31, 0.37 mmol of the complex of Example 4 and 0.7 mmol of PPh3 added separately in Example 32, 1 g of 5% palladium supported on carbon without any phosphine ligand in Example J, and 8.4 mmol of PdCl$_2$ without any phosphine ligand in Example I. No catalyst at all was used in Example H. In place of HBr, 25 g of 10% HCl was the acid used in Example J, and the solvent was 27 ml of benzene in Examples I and J. In Example I, 0.6 mmol of t-butylcatechol was added while 3.2 mmol of p-mercaptoacetophenone were added in Example J. The results are shown in Table VII.

TABLE VII

| Example | Conv. % | Percent Selectivity | | | |
|---|---|---|---|---|---|
| | | Ibuprofen | 3-IPPA | IBS | HE |
| 31 | 99 | 62 | 19 | tr | 11 |
| 32 | 99 | 51 | 20 | tr | 10 |
| H | 72 | 0 | 0 | 44 | 38 |
| I | 96 | tr | 0 | 86 | 13 |
| J | 94 | 25 | 2 | 14 | 17 |

The results of Table VII indicate that the phosphine ligand may be added separately with the palladium compound to obtain a satisfactory yield of ibuprofen, but that a palladium catalyst with an appropriate ligand other than CO is required in order to obtain satisfactory yields of ibuprofen. This is illustrated by the results of Examples 3I and 32 as compared with those of Comparative Examples H, I, and J wherein no catalyst at all was utilized in Example H, and no phosphine ligand was employed in Examples I and J. Examples 33 and 34 illustrate the employment of higher and lower reaction temperatures than was employed in the previous examples.

EXAMPLES 33 AND 34

The procedure of Example 16 was followed except that the reaction time was 6 h and the reaction temperature was 150° C. in Example 33 and 100° C in Example 34. The results are shown in Table VIII.

TABLE VIII

| Example | Conv., % | Percent Selectivity | | | |
|---|---|---|---|---|---|
| | | Ibuprofen | 3-IPPA | IBS | HE |
| 33 | 99 | 75 | 18 | tr | 6 |
| 34 | 99 | 69 | 11 | tr | 8 |

Examples 35 to 38 illustrate the employment of operable CO pressures higher and lower than that employed in the previous examples.

EXAMPLES 35 to 38

The procedure of Example 16 was followed except that the pressure was varied in each example. The pressures employed and the results obtained are shown in Table IX.

TABLE IX

| Example | Pressure, psig | Conv., % | Percent Selectivity | | | |
|---|---|---|---|---|---|---|
| | | | Ibuprofen | 3-IPPA | IBS | HE |
| 35 | 1200 | 99 | 71 | 12 | 0 | 9 |
| 36 | 1000 | 99 | 69 | 16 | 0 | 4 |
| 37 | 700 | 99 | 74 | 12 | tr | 11 |
| 38 | 600 | 99 | 58 | 16 | tr | 13 |

Examples 39 to 41 illustrate the recharging of additional quantities of IBPE after the initial reaction is commenced.

EXAMPLES 39 to 41

The procedure of Example 16 was followed except that in Example 39, 27 ml of acetone rather than methyl ethyl ketone was used as solvent, and after the addition of the initial 56 mmol of IBPE, 196.8 mmol of additional IBPE were added over a 30 min. period, and the total reaction time was 4.3 h. In Example 40 an additional 56 mmol of IBPE were added over a 1 h period after the introduction of the initial 56 mmol, and the total reaction time was 6.5 h. Example 41 was similar to Example 40 except that the solvent was 27 g of acetone and the total reaction time was 7 h. The results are shown in Table X.

TABLE X

| Example | Conv., % | Percent Selectivity | | | |
|---|---|---|---|---|---|
| | | Ibuprofen | 3-IPPA | IBS | HE |
| 39 | 99 | 48 | 16 | 18 | 9 |
| 40 | 99 | 80 | 19 | tr | 5 |
| 41 | 99 | 73 | 20 | 2 | 13 |

The results of Examples 39 to 41 indicate that after the initial charging of IBPE, an additional quantity of IBPE may be added to the reaction, without reducing the yield of ibuprofen to an undesirably low level.

EXAMPLES 42 to 50

These examples illustrate the production of ibuprofen by the carbonylation of IBPE with different loadings of PdCl$_2$(PPh$_3$)$_2$ as catalyst relative to IBPE, and with varying CO pressures.

The examples were carried out using a 300 ml autoclave to which were added 112 mmol of IBPE, 54 ml of methyl ethyl ketone (MEK) as added organic solvent, 50 g of 10% aqueous HCl (resulting in constant mole ratios of H+/IPBE=1.22 and H$_3$O/H$_2$O=0.055), and varying amounts of catalyst. The autoclave was pressured with CO to a level sufficient to result in the targeted reaction pressure at the temperature of reaction. The contents were then heated to such temperature which in these examples was 125° C. and CO was fed to the reactor to maintain the desired pressure as the CO was absorbed during the reaction. The reaction temperature was maintained for the desired reaction time with vigorous stirring. The amount of catalyst in millimoles (Cat.), the resulting mole ratios of palladium to IBPE (Pd:IBPE) and reaction times and pressures as well as the results of the reaction in terms of percent IBPE conversion (Conv.) and percent selectivities to ibuprofen (IBU), 3-(4'-isobutylphenyl)propionic acid (3-IPPA), 4-isobutylstyrene (IBS) and heavy ends (HE), are shown in Table XI. These results and those of subsequent examples were determined by GLC which are susceptible to errors of about ±5%. This explains why some individual selectivities and/or the sums of selectivities in some examples are above 100%.

TABLE XI

| Example | Cat. mmol | Pd:IBPE | Time, h | Press., psig | Conv., % | Percent Selectivity | | | |
|---|---|---|---|---|---|---|---|---|---|
| | | | | | | IBU | 3-IPPA | IBS | HE |
| 42 | 0.185 | 1:605 | 6 | 1000 | 99 | 89.7 | 7.6 | <1 | 7.2 |
| 43 | 0.185 | 1:605 | 6 | 1000 | 99 | 98.4 | 7.3 | <1 | 3.0 |
| 44 | 0.076 | 1:1474 | 3 | 1000 | 96 | 76.2 | 0.76 | 14.8 | 3.8 |
| 45 | 0.095 | 1:1179 | 3 | 1000 | 99 | 83.3 | 1.8 | 4.2 | 3.2 |
| 46 | 0.076 | 1:1474 | 3 | 1300 | 98 | 79.2 | 0.6 | 8.3 | 3.6 |
| 47 | 0.076 | 1:1474 | 3 | 1500 | 98 | 78.6 | 0.6 | 9.1 | 3.6 |
| 48 | 0.076 | 1:1474 | 3 | 2000 | 99 | 87.9 | 0.7 | 0.8 | 0.7 |
| 49 | 0.076 | 1:1474 | 3 | 2000 | 99 | 96.6 | 0.9 | 0.4 | 1.4 |
| 50 | 0.076 | 1:1474 | 3 | 3100 | 99 | 99.1 | 0.7 | 0.1 | 1.0 |

EXAMPLES 51 to 61

These examples illustrate the employment of varying ratios of hydrogen ion and palladium to IBPE in the production of ibuprofen by the carbonylation of IBPE.

The general procedure of Examples 42 to 50 was followed using 54 mL of MEK as added organic solvent and varying amounts of IBPE and catalyst, either 25 g of 20% HCl (H$_3$O$^{30}$/H$_2$O=0.124) or 50 g of 10% HCl (H$_3$O/H$_2$O=0.055), and varying pressures and reaction times. Reaction conditions and results are shown in Table XII.

TABLE XII

| Example | IBPE, mmol. | HCl, %/g | H+/IBPE | Cat., mmol | Pd:IBPE | Time, h | Press. psig | Conv., % | Percent Selectivity | | | |
|---|---|---|---|---|---|---|---|---|---|---|---|---|
| | | | | | | | | | IBU | 3-IPPA | IBS | HE |
| 51 | 112.0 | 20/25 | 1.22 | 0.076 | 1:1474 | 3 | 2000 | 97 | 89.0 | 0.5 | 1.1 | 1.2 |
| 52 | 224.0 | 20/25 | 0.61 | 0.173 | 1:1295 | 2 | 1850 | 99 | 96.8 | 1.6 | 0.2 | 0.6 |
| 53 | 336.0 | 20/25 | 0.41 | 0.260 | 1:1292 | 2 | 1750 | 99 | 97.3 | 2.3 | 0.1 | 0.9 |
| 54 | 336.0 | 20/25 | 0.41 | 0.260 | 1:1292 | 2 | 2000 | 99 | 92.9 | 1.6 | 0.1 | 0.6 |
| 55 | 168.0 | 10/50 | 0.82 | 0.076 | 1:2211 | 3 | 2000 | 94 | 41.9 | 0.3 | 29.9 | 9.6 |
| 56 | 224.0 | 10/50 | 0.62 | 0.185 | 1:1211 | 2 | 2000 | 99 | 101.3 | 1.5 | 0.2 | 1.4 |
| 57 | 336.0 | 10/50 | 0.41 | 0.260 | 1:1292 | 2 | 4750 | 84 | 60.2 | 0.5 | 1.2 | 48.6 |
| 58 | 336.0 | 10/50 | 0.41 | 0.260 | 1:1292 | 2 | 2000 | 93 | 73.7 | 2.1 | 0.6 | 21.1 |
| 59 | 336.0 | 10/50 | 0.41 | 0.260 | 1:1292 | 2 | 3100 | 99 | 92.1 | 1.7 | 0.1 | 1.1 |
| 60 | 336.0 | 10/50 | 0.41 | 0.260 | 1:1292 | 2 | 3000 | 94 | 74.6 | 1.2 | 0.9 | 17.8 |
| 61 | 336.0 | 10/50 | 0.41 | 0.260 | 1:1292 | 2 | 4550 | 99 | 102.3 | 1.2 | 0.4 | 2.9 |

EXAMPLES 62 to 66

These examples illustrate the production of ibuprofen by the carbonylation of IBPE without the employment of any added organic solvent.

The procedure of Examples 42 to 61 was followed using 336.0 mmol of IBPE, either 25 g of 20% HCl (H./IBPE=0.41, H$_3$O+/H$_2$O=0.124) or 14 g of 36% HCl (H /IBPE=0.41, H$_3$O×/ H$_2$O=0.278), 0.260 mmol of catalyst (pd:IBPE=1:1292), and no added organic solvent. The reaction temperature was 125° C and the reaction time was 2 hours. Other reaction conditions and results are shown in Table XIII.

TABLE XIII

| Example | HCl, %/g | Press., psig | Conv. % | Percent Selectivity | | | |
|---|---|---|---|---|---|---|---|
| | | | | IBU | 3-IPPA | IBS | HE |
| 62 | 20/25 | 2000 | 98 | 41.1 | 1.7 | 1.4 | 38.2 |
| 63 | 20/25 | 2000 | 99 | 94.8 | 3.1 | 0.2 | 1.2 |
| 64 | 20/25 | 3000 | 99 | 62.8 | 1.8 | 1.1 | 25.1 |
| 65 | 36/14 | 2000 | 99 | 52.2 | 2.1 | 2.1 | 20.2 |
| 66 | 36/14 | 2000 | 99 | 77.9 | 2.9 | 1.4 | 9.2 |

EXAMPLES 67 to 70

These are additional examples illustrating the suitability of hydrobromic acid as a source of hydrogen and halide ions both in the presence and absence of added organic solvent in the preparation of ibuprofen by the carbonylation of IBPE.

The general procedure of Examples 42 to 66 was followed using varying amounts IBPE and MEK solvent (including none), 16.2% HBr ($H_3O^+/H_2O=0.043$) or 20% HBr ($H_3O^+/H_2O=0.056$) and catalyst. The reaction temperature was 125° C. The conditions of reaction and results are shown in Table XIV.

EXAMPLES 76 to 98

These examples illustrate the method of making ibuprofen by the carbonylation if IBPE under the invention using a 4 liter autoclave and varying conditions of reaction including higher mole ratios of Pd to phosphine ligand and concentrations of HCl as low as 5% ($H_3O^+/H_2O=0.026$).

The general procedure of Examples 42 to 70 was followed in a 4 liter autoclave using HCl as the acid and MEK as solvent or no solvent, except that the catalyst was added as separate quantities of palladium dichloride, $PdCl_2$ and triphenylphosphine, $PPh_3$, such that the

TABLE XIV

| Example | IBPE mmol. | MEK, mL | HBr, %/g | H+/ IBPE | Cat., mmol | Pd:IBPE | Time h | Press. psig | Percent Selectivity | | | |
|---|---|---|---|---|---|---|---|---|---|---|---|---|
| | | | | | | | | | IBU | 3-IPPA | IBS | HE |
| 67 | 56.0 | 27 | 16.2/25 | 0.89 | 0.37 | 1:151 | 6 | 1000 | 69.3 | 24.4 | <1 | 11.8 |
| 68 | 112.0 | 54 | 16.2/50 | 0.89 | 0.076 | 1:1474 | 3 | 1000 | 78.0 | 9.7 | — | 6.2 |
| 69 | 336.0 | 0 | 20/55.5 | 0.41 | 0.260 | 1:1292 | 2 | 2000 | 68.7 | 2.1 | 0.3 | 12.1 |
| 70 | 336.0 | 0 | 20/55.5 | 0.41 | 0.260 | 1:1292 | 2 | 2000 | 80.7 | 2.4 | 0.2 | 4.3 |

EXAMPLES 71 TO 75

The examples illustrate the method under the invention of making ibuprofen by the carbonylation of IBPE using at least one specific condition which is somewhat different than those shown in Examples 42 to 70 including a reaction temperature of 140° C. (Examples 71 and 72) an amount of hydrogen nearer the lower limit of the invention (Examples 73, 74 and 75), the use of 11% HCl ($H_3O^+/H_2O=0.061$) and the use of dioxane (DIOX) as a solvent (Examples 74 and 75). The general procedure of Examples 42 to 70 was followed using specific conditions including those described in the preceding paragraph. Such conditions and the results are shown in Table XV.

Pd:P ratio was varied within the disclosed limits. The specific conditions of reaction, including the mole ratios of palladium to phosphine to IBPE (Pd:P:IBPE), are shown in Table XVI.

TABLE XVI

| Expl | IBPE mmol | MEK, ml | HCl, %/ml | H+/ IBPE | PdCl₂, mmol | PPh₃, mmol | Pd: P:IBPE | Temp. °C. | Time, h:min | Press. psig | Conv. % | Percent Selectivity | | | |
|---|---|---|---|---|---|---|---|---|---|---|---|---|---|---|---|
| | | | | | | | | | | | | IBU | 3-IPPA | IBS | HE |
| 76 | 1685.0 | 840 | 10/750 | 1.3 | 2.8 | 8.6 | 1:3:602 | 130 | 0:50 | 1000 | 99 | 92.1 | 7.7 | <1 | 1.4 |
| 77 | 1685.0 | 840 | 10/750 | 1.3 | 2.8 | 8.6 | 1:3:602 | 130 | 1:20 | 1000 | 99 | 78.7 | 8.7 | <1 | 2.0 |
| 78 | 3370.0 | 840 | 10/750 | 0.7 | 2.8 | 8.6 | 1:3:1204 | 130 | 1:35 | 2000 | 98 | 89.6 | 2.2 | 0.2 | 0.1 |
| 79 | 3370.0 | 840 | 20/375 | 0.66 | 2.8 | 8.6 | 1:3:1204 | 130 | 1:30 | 2000 | 99 | 93.9 | 2.3 | 0.2 | 0.1 |
| 80 | 3370.0 | 420 | 20/375 | 0.66 | 2.8 | 8.6 | 1:3:1204 | 130 | 1:20 | 2000 | 99 | 92.8 | 2.9 | 0.2 | 0.1 |
| 81 | 5056.0 | 0 | 20/375 | 0.44 | 2.8 | 8.6 | 1:3:1806 | 150 | 0:40 | 2000 | 99 | 83.4 | 4.9 | 0.3 | 0.1 |
| 82 | 5056.0 | 0 | 20/375 | 0.44 | 2.8 | 8.6 | 1:3:1806 | 130 | 2:45 | 2000 | 99 | 80.2 | 3.6 | 1.2 | 3.9 |
| 83 | 6742.0 | 0 | 20/525 | 0.47 | 4.0 | 12.0 | 1:3:1686 | 130 | 2:30 | 2000 | 99 | 85.3 | 4.3 | 0.3 | 3.3 |
| 84 | 6742.0 | 0 | 20/525 | 0.47 | 4.0 | 12.0 | 1:3:1686 | 130 | 2:0 | 2400 | 99 | 93.5 | 4.0 | 0.1 | 1.1 |
| 85 | 6742.0 | 0 | 20/525 | 0.47 | 2.3 | 9.5 | 1:4:2931 | 130 | 2:10 | 2400 | 99 | 91.1 | 3.1 | 0.3 | 1.6 |
| 86 | 8426.0 | 0 | 20/525 | 0.38 | 2.8 | 8.8 | 1:3:3010 | 130 | 2:45 | 2400 | 99 | 86.4 | 2.1 | 0.2 | 1.5 |
| 87 | 8427.0 | 0 | 36/525 | 0.74 | 2.8 | 8.8 | 1:3:3010 | 130 | 2:15 | 2400 | 99 | 89.3 | 1.0 | 0.4 | 1.5 |
| 88 | 9831.0 | 0 | 36/300 | 0.36 | 3.4 | 10.3 | 1:3:2891 | 130 | 3:0 | 2400 | 99 | 86.2 | 1.3 | 0.2 | 0.7 |
| 89 | 2247.0 | 880 | 20/190 | 0.51 | 0.90 | 9.2 | 1:10:2497 | 150 | 2:15 | 1000 | 99 | 89.9 | 4.5 | 0.2 | 2.0 |
| 90 | 2247.0 | 1670 | 5/300 | 0.20 | 0.90 | 9.2 | 1:10:2497 | 150 | 2:35 | 1000 | 98 | 55.9 | 4.7 | 7.1 | 7.2 |
| 91 | 2247.0 | 1670 | 5/300 | 0.20 | 0.9 | 9.2 | 1:10:2497 | 150 | 2:30 | 1000 | 98 | 74.8 | 6.2 | 9.1 | 1.0 |
| 92 | 2247.0 | 1000 | 20/75 | 0.20 | 9.0 | 90.5 | 1:10:250 | 150 | 3:0 | 2000 | 99 | 57.9 | 21.6 | 1.0 | 13.7 |
| 93 | 2247.0 | 1220 | 5/750 | 0.48 | 9.0 | 90.5 | 1:10:250 | 130 | 2:15 | 2000 | 99 | 69.4 | 22.0 | 0.9 | 4.4 |
| 94 | 2247.0 | 770 | 5/300 | 0.20 | 9.0 | 17.9 | 1:2:250 | 130 | 2:00 | 1000 | 98 | 71.2 | 21.3 | 1.3 | 7.6 |
| 95 | 2247.0 | 1900 | 20/75 | 0.20 | 0.90 | 1.9 | 1:2:2497 | 130 | 5:00 | 2000 | 99 | 75.6 | 0.2 | 1.2 | 9.2 |
| 96 | 5056.0 | 0 | 20/530 | 0.63 | 2.54 | 1.9 | 1:2:2497 | 130 | 5:00 | 2000 | 99 | 56.9 | 0.2 | 0.6 | 14.5 |
| 97 | 5056.0 | 0 | 20/530 | 0.63 | 2.54 | 67.7 | 1:27:1991 | 130 | 3:00 | 2000 | 99 | 76.1 | 13.1 | 0.7 | 0.1 |
| 98 | 5056.0 | 0 | 0/1230 | 0.62 | 2.54 | 68.7 | 1:27:1991 | 130 | 3:00 | 2400 | 99 | 68.2 | 19.6 | 0.8 | 9.4 |

EXAMPLES 99 TO 105

These examples illustrate that excellent IBPE conversions and ibuprofen selectivities can be obtained using particularly low Pd:P and Pd:IBPE mole ratios.

The general procedure was similar to that of Examples 76 to 98 using the following specific conditions: the 4 liter autoclave was charged with 8.43 mole of IBPE

TABLE XV

| Example | IBPE mmol | Solvent ml | HCl %/g | H+/ IBPE | Cat., mmol | Pd: IBPE | Temp., °C. | Time, h | Press., psig | Conv., % | Percent Selectivity | | | |
|---|---|---|---|---|---|---|---|---|---|---|---|---|---|---|
| | | | | | | | | | | | IBU | 3-IPPA | IBS | HE |
| 71 | 336.0 | MEK/54 | 20/25 | 0.41 | 0.260 | 1:1292 | 140 | 2 | 2000 | 97 | 69.9 | 0.7 | 0.6 | 4.7 |
| 72 | 336.0 | MEK/54 | 20/25 | 0.41 | 0.260 | 1:1292 | 140 | 2 | 2000 | 99 | 95.5 | 2.5 | 0.1 | 0.5 |
| 73 | 336.0 | MEK/54 | 20/10 | 0.16 | 0.260 | 1:1292 | 125 | 2 | 2000 | 94 | 85.0 | 1.1 | 2.6 | 5.7 |
| 74 | 132.4 | DIOX/93 | 11/9 | 0.20 | 0.188 | 1:704 | 125 | 6 | 1000 | 99 | 82.8 | 1.0 | 0.2 | 0.1 |
| 75 | 132.4 | DIOX/93 | 11/9 | 0.20 | 0.188 | 1:704 | 125 | 6 | 500 | 99 | 42.6 | 1.9 | 0.2 | 0.2 | and 775 ml of 26% HCl (e₃O+/H₂O =0.173) for a H/IBPE mole ratio of 0.75. No solvent was used. The temperature of the reaction was 130° C. Process conditions which were varied and the results of the examples are shown in Table XVII.

TABLE XVII

| Example | Exp. No. | PdCl$_2$, mmol | PPh$_3$, mmol | Pd:P:IBPE | Time, h:min | Press., psig | Conv., % | Percent Selectivity ||||
|---|---|---|---|---|---|---|---|---|---|---|---|
| | | | | | | | | IBU | 3-IPPA | IBS | HE |
| 99 | 36298-43 | 0.56 | 6.9 | 1:12:15050 | 3:00 | 2400 | 99 | 95.8 | 0.8 | 0.0 | 0.9 |
| 100 | 36298-44 | 0.56 | 6.9 | 1:12:15050 | 2:35 | 2400 | 99 | 96.6 | 1.0 | 0.0 | 0.8 |
| 101 | 36298-45 | 0.56 | 6.9 | 1:12:15050 | 4:00 | 2400 | 99 | 95.7 | 0.8 | 0.0 | 0.6 |
| 102 | 36298-46 | 1.12 | 6.9 | 1:6:7524 | 4.00 | 2400 | 99 | 95.1 | 1.1 | 0.0 | 0.7 |
| 103 | 36298-49 | 0.56 | 6.9 | 1:12:15050 | 4:00 | 1500 | 99 | 91.5 | 1.2 | 0.1 | 1.3 |
| 104 | 36320-04 | 0.56 | 13.8 | 1:24:15050 | 4:00 | 1500 | 99 | 91.9 | 1.9 | 0.1 | 1.2 |
| 105 | 36320-07 | 0.28 | 6.9 | 1:24:30100 | 4:00 | 2400 | 99 | 79.5 | 0.7 | 1.0 | 6.8 |

Examples K and L were carried out under conditions similar to those of the Comparative Example 11 of Japanese Kokai Patent No. SHO 59 [1984]-95238, involving ibuprofen as a product.

EXAMPLE K

The procedure of Examples 42 to 75 using the 300 mL autoclave was followed except that the starting material was 84.3 mmol of IBPE, the acid was 8% HCl (4.0 g, 8.8 mmol), for a H+/IBPE mole ratio of 0.10, 0.471 mmol of catalyst was used, the solvent was 61 g of dioxane, the CO pressure was 1700 psig, the reaction temperature was 110° C., and the reaction time was 5.5 h. The IBPE conversion was 60% and the product selectivities were ibuprofen 38.6%, 3-IPPA 1.4%, IBS 2.4%, and HE 59.3%.

EXAMPLE L

The procedure of Example K was followed except that 112 mmol of IBPE, 6 g of 8% HCl (H+/IPBE=0.10) and 82 g of dioxane were utilized. The IBPE conversion was 68% and the selectivities were ibuprofen 42.0%, 3-IPPA 0.1%, IBS 2.1% and HE 43.5%.

The results of Examples K and L confirm that the conditions of the Japanese patent, which include the presence of dissociated hydrogen and halide ions in amounts considerably below the minimums required in the method of this invention, result in comparatively very low yields of ibuprofen.

Example 106 which follows, relates particularly to the recovery and recycling of nobel metal catalyst complexes useful in the production method.

EXAMPLE 106

The following ingredients were added to a 4 liter autoclave: 300 g (1.69 mole) 1-(4'-isobutylphenyl)ethanol, 840 ml methylethylketone, 2 g (0.0113 mole) palladium (II) chloride, 9 g (0.0344 mole) triphenyl phosphine, 38 g (0.34 mole) calcium chloride, 203 ml 36% HCl, 547 ml water. After flushing with nitrogen and carbon monoxide, the autoclave was pressured to approximately 700 psig of carbon monoxide. The reactor was stirred and heated to 130° C during which time the pressure inside the reactor increased to approximately 1000 psig and was subsequently maintained at this pressure during the 2 hour reaction time. After the carbon monoxide uptake was complete the reactor was cooled to room temperature and vented. The contents of the reactor were removed and the two phases were separated in a separatory funnel. The aqueous phase was extracted with 500 ml ethyl acetate and the organic fractions were combined and the solvents removed on a rotary evaporator under reduced pressure. During evaporation 6.4 g (81% of theoretical) yellow crystalline PdCl$_2$ PPH$_3$) suitable for reuse, precipitated and was recovered. 0.2 g (16% of theoretical) of palladium metal was recovered by filtration of the aqueous phase.

The organic product obtained was 348 g and contained 57% ibuprofen.

We claim:

1. A method of preparing ibuprofen comprising carbonylating 1-(4,-isobutylphenyl)ethanol (IBPE) with carbon monoxide in an acidic aqueous medium, at a temperature of at least about 10° C. and a carbon monoxide pressure of at least about 500 psig, and in the presence of (1) a catalyst consisting essentially of a palladium compound in which the palladium has a valence of zero to 2 and is complexed with at least one acid stable, monodentate phosphine ligand miscible with the organic phase of the reaction medium, the phosphorus/palladium mole ratio in said palladium compound and ligand being at least about 2:1 when the mole ratio of palladium to IBPE is such that palladium=1 and IBPE=10,000 or more; (2) dissociated hydrogen ions from an acid which is substantially completely ionizable in a dilute aqueous solution such that the mole ratio of hydrogen ions to IBPE added to the reaction zone is at least about 0.15, and; (3) dissociated halide ions such that the mole ratio of halide ions to IBPE added to the reaction zone is at least about 0.15.

2. The method of claim 1 wherein said ligand is a tri(organo) phosphine.

3. The method of claim 2 wherein said ligand is triphenyl phosphine.

4. The method of claim 3 wherein said catalyst is a palladium bis(triphenyl phosphine) dichloro complex.

5. The method of claim 1 wherein the source of said hydrogen ions and halide ions is a hydrogen halide.

6. The method of claim 5 wherein said hydrogen halide is hydrogen chloride.

7. The method of claim 5 wherein said hydrogen halide is hydrogen bromide.

8. The method of claim 1 wherein an organic solvent is present during said carbonylation, said solvent being a nonhydrocarbon if said palladium is added to the system in a zero valence state.

9. The method of claim 8 wherein said organic solvent is a ketone.

10. The method of claim 9 wherein said ketone is methyl ethyl ketone.

11. The method of claim 1 wherein the mole ratio of palladium to IBPE is from about 1:25 to 1:60,000.

12. The method of claim 11 wherein said mole ratio of palladium to IBPE is from about 1:10,000 to 1:40,000.

13. A method of producing ibuprofen comprising reacting isobutylbenzene with an acetylating agent in the presence of a Friedel-Crafts catalyst to produce 4'-isobutylacetophenone (IBAP), reducing said IBAP with hydrogen in the presence of a hydrogenation catalyst, or with a reducing agent containing available hydrogen, to obtain 1-(4'-isobutylphenyl)ethanol (IBPE), carbonylating said IBPE with carbon monoxide in an acidic aqueous medium at a temperature of at least about 10° C. and a carbon monoxide pressure of at least about 500 psig, and in the presence of (1) a catalyst consisting essentially of a palladium compound in which the palladium has a valence of zero to 2 and is complexed with at least one acid stable, monodentate phosphine ligand miscible with the organic phase of the reaction medium, the phosphorus/palladium mole ratio in said palladium compound and ligand being at least about 2:1 when the mole ratio of palladium to IBPE is such that palladium=1 and IBPE=10,000 or more; (2) dissociated hydrogen ions from an acid which is substantially completely ionizable in dilute aqueous solution such that the mole ratio of hydrogen ions to IBPE added to the reaction zone is at least about 0.15; and, (3) dissociated halide ions such that the mole ratio of halide ions to IBPE added to the reaction zone is at least about 0.15.

14. The method of claim 13 wherein said catalyst is a palladium bis(triphenylphosphine) dichloro complex.

15. The method of claim 13 wherein the source of said hydrogen ions and halide ions is a hydrogen halide.

16. The method of claim 15 wherein said source is hydrogen chloride.

17. The method of claim 15 wherein said source is hydrogen bromide.

18. The method of claim 13 wherein an organic solvent is present during said carbonylation, said solvent being a nonhydrocarbon, if said palladium is added to the system in the zero valence state.

19. The method of claim 18 wherein said organic solvent is methyl ethyl ketone.

20. The method of claim 13 wherein the mole ratio of palladium to IBPE is from about 1:25 to 1:60,000.

21. The method of claim 20 wherein said mole ratio of palladium to IBPE is from about 1:10,000 to 1:40,000.

22. A method of preparing ibuprofen comprising carbonylating 1-(4-isobutylphenyl)ethanol (IBPE) with carbon monoxide in an acidic aqueous medium, at a temperature of at least about 10° C. and a carbon monoxide pressure of at least about 500 psig, and in the presence of a catalyst consisting essentially of a palladium bis(triphenylphosphine) dichloro complex, dissociated hydrogen and chloride ions from hydrogen chloride such that the mole ratio of each of said hydrogen and chloride ions to IBPE added is at least about 0.2, and an organic solvent in an amount such that the weight ratio of solvent to IBPE is at least about 1.5.

23. The method of claim 1, 13, or 22, wherein a palladium-containing catalyst complex is recovered by precipitating said complex from an organic phase formed during said carbonylation, wherein said organic phase contains ibuprofen product.

24. The method of claim 1 or 13 wherein an organic solvent is used as part of the reaction medium and wherein a palladium-containing catalyst complex is recovered by precipitating said complex from an organic phase formed during said carbonylation.

25. The method of claim 23 wherein said organic phase is separated from said aqueous medium prior to precipitation of said catalyst complex, and wherein said aqueous medium contains dissociated hydrogen and halide ions.

26. The method of claim 24 wherein said organic phase is separated from said aqueous medium prior to precipitation of said catalyst complex, and wherein said aqueous medium contains dissociated hydrogen and halide ions.

27. The method of claim 25 wherein an organic agent is added to said reaction medium to improve the phase separation between said organic and said aqueous phases.

28. The method of claim 26 wherein an organic agent is added to said reaction medium to improve the phase separation between said organic and said aqueous phases.

29. The method of claim 27 wherein said organic agent is removed to facilitate precipitation of said catalyst complex.

30. The method of claim 28 wherein said organic agent is removed to facilitate precipitation of said catalyst complex.

* * * * *

UNITED STATES PATENT AND TRADEMARK OFFICE
CERTIFICATE OF CORRECTION

PATENT NO. : 4,981,995
DATED : January 1, 1991
INVENTOR(S) : Elango et al.

It is certified that error appears in the above—identified patent and that said Letters Patent is hereby corrected as shown below:

On the cover page, the following Assignee should be present:

[73] Assignee: HOECHST CELANESE CORPORATION
Somerville, New Jersey

On the cover page, the following Related U. S. Application Data should be present:

[63] Related U. S. Application Data
Continuation In Part of Ser. No. 357,381, May 24, 1989, abandoned; which was a Continuation In Part of Ser. No. 158,141, March 4, 1988, abandoned; which was a Continuation In Part of Ser. No. 028,514, March 20, 1987, abandoned. Also a Continuation In Part of Ser. No. 182,263, April 15, 1988, abandoned.

On the cover page under [56] FOREIGN PATENT DOCUMENTS

Delete "2242642   10/1982 Japan" and insert
-- JP59 - 95238   6/1984 Japan -- .

Delete "2242641   10/1987 Japan" and insert
-- JP59 - 95239   6/1984 Japan -- .

Delete "2263140   11/1987 Japan" and insert
-- 219752   9/1985 Czechoslovakia -- .

Col. 3, line 29, prior to "preferably", delete "225.C" and
insert -- 225°C -- .

Col. 3, line 29, prior to "the", delete "175.C" and
insert -- 170°C -- .

UNITED STATES PATENT AND TRADEMARK OFFICE
CERTIFICATE OF CORRECTION

PATENT NO.   : 4,981,995
DATED        : January 1, 1991
INVENTOR(S)  : Elango et al.

It is certified that error appears in the above-identified patent and that said Letters Patent is hereby corrected as shown below:

Col. 8, line 24, prior to "In", delete "70.C to 80.C" and
insert -- 70°C to 80°C -- .

Col. 8, line 30, prior to "and", delete "25.C to 90.C" and
insert -- 25°C to 90°C -- .

Col. 9, line 36, prior to "under", delete "30.C" and
insert -- 30°C -- .

Col. 9, line 67, after "at", delete "70.C" and
insert -- 70°C -- .

Col. 10, line 39, delete "N-7043C".

Col. 12, line 11, prior to "was", delete "H$_3$0/H$_2$0 = 0.065)" and
insert -- H$_3$0$^+$/H$_2$0 = 0.065) -- .

Col. 15, line 51, prior to "and", delete " H$_3$0/H$_2$0 = 0.055 " and
insert -- H$_3$0$^+$/H$_2$0 = 0.055) -- .

Col. 16, line 24, after "HCl", delete "(H$_3$0$^{30}$/H$_2$0 = 0.124)" and
insert -- (H$_3$0$^+$/H$_2$0 = 0.124) -- .

Col. 16, line 25, prior to ",and", delete "(H$_3$0/H$_2$0 = 0.055)" and
insert -- (H$_3$0$^+$/H$_2$0 = 0.055) -- .

Col. 16, line 54, prior to "or", delete "(H./IBPE = 0.41, H$_3$0$^+$/H$_2$0 = 0.124)" and
insert -- (H$^+$/IBPE = 0.41, H$_3$0$^+$/H$_2$0 = 0.124) -- .

Col. 16, line 55, prior to ", 0.260", delete "(H/IBPE = 0.41, H$_3$0$^x$/H$_2$0 = 0.278)" and
insert -- (H$^+$/IBPE = 0.41, H$_3$0$^+$/H$_2$0 = 0.278) -- .

UNITED STATES PATENT AND TRADEMARK OFFICE
CERTIFICATE OF CORRECTION

PATENT NO. : 4,981,995
DATED : January 1, 1991
INVENTOR(S) : Elango et al.

It is certified that error appears in the above—identified patent and that said Letters Patent is hereby corrected as shown below:

Col. 17, line 10, after "HBr", delete "($H_3O^*H_2O = 0.043$)" and
insert -- ($H_3O^+/H_2O = 0.043$) -- .

Col. 17, line 11, prior to "and", delete "($H_3O^{+H}_2O = 0.056$)" and
insert -- ($H_3O^+/H_2O = 0.056$) -- .

Col. 17, line 54, prior to "and", delete "($H_3O_./H_2O = 0.06I$)" and
insert -- ($H_3O^+/H_2O = 0.061$) -- .

Col. 19, line 1, after "HCl", delete "($e_3O^+/H_2O = 0.173$)" and
insert -- ($H_3O^+/H_2O = 0.173$) -- .

Col. 19, line 36, after "HCl", delete "($H^+/IP$-" and
insert -- ($H^+/IB$- -- .

Col. 19, line 36, prior to "and", delete "BE = 0.10)" and
insert -- PE = 0.10) -- .

UNITED STATES PATENT AND TRADEMARK OFFICE
CERTIFICATE OF CORRECTION

PATENT NO. : 4,981,995

DATED : January 1, 1991

INVENTOR(S) : Varadaraj Elango, et al.

It is certified that error appears in the above-identified patent and that said Letters Patent is hereby corrected as shown below:

Col. 21, line 11, prior to "mole", delete "phosphorus/palladium" and insert -- phosphorus : palladium -- .

Signed and Sealed this

Fifteenth Day of December, 1992

*Attest:*

DOUGLAS B. COMER

*Attesting Officer*      *Acting Commissioner of Patents and Trademarks*